(12) United States Patent
Brubaker et al.

(10) Patent No.: US 12,121,670 B1
(45) Date of Patent: Oct. 22, 2024

(54) CATHETER SYSTEM

(71) Applicants: William Brubaker, Palo Alto, CA (US); Paul Davis, Los Altos Hills, CA (US)

(72) Inventors: William Brubaker, Palo Alto, CA (US); Paul Davis, Los Altos Hills, CA (US)

( * ) Notice: Subject to any disclaimer, the term of this patent is extended or adjusted under 35 U.S.C. 154(b) by 0 days.

(21) Appl. No.: 18/208,064

(22) Filed: Jun. 9, 2023

(51) Int. Cl.
| | | |
|---|---|---|
| *A61M 25/00* | (2006.01) | |
| *A61F 5/44* | (2006.01) | |
| *A61M 25/01* | (2006.01) | |
| *A61M 25/10* | (2013.01) | |
| *A61M 39/10* | (2006.01) | |

(52) U.S. Cl.
CPC ...... *A61M 25/0017* (2013.01); *A61M 25/002* (2013.01); *A61M 25/0043* (2013.01); *A61M 25/0045* (2013.01); *A61M 25/0111* (2013.01); *A61M 25/1006* (2013.01); *A61M 25/1018* (2013.01); *A61M 39/10* (2013.01); *A61F 5/44* (2013.01); *A61M 25/00* (2013.01); *A61M 2025/0046* (2013.01); *A61M 2025/0056* (2013.01); *A61M 2210/1089* (2013.01)

(58) Field of Classification Search
CPC ............ A61M 25/0017; A61M 25/002; A61M 2210/1085; A61M 2202/0496; A61M 2210/1089; A61M 25/00; A61M 25/0075; A61M 39/10; A61M 25/01; A61M 25/02; A61M 2210/1078; A61F 5/44; A61F 5/4405; A61F 5/453; A61F 5/451
See application file for complete search history.

(56) References Cited

U.S. PATENT DOCUMENTS

| | | | | | |
|---|---|---|---|---|---|
| 3,661,143 | A | * | 5/1972 | Henkin | A61F 5/441 600/580 |
| 4,029,099 | A | * | 6/1977 | Fifield | A61M 39/08 604/326 |
| 4,319,573 | A | * | 3/1982 | Whitlock | A61F 5/44 604/323 |
| 4,421,509 | A | * | 12/1983 | Schneider | A61F 5/4408 604/327 |
| 4,483,688 | A | * | 11/1984 | Akiyama | A61M 25/0017 604/326 |
| 4,583,967 | A | * | 4/1986 | Harris | A61M 27/006 604/9 |

(Continued)

FOREIGN PATENT DOCUMENTS

| | | | | | |
|---|---|---|---|---|---|
| EP | 0108736 | A1 * | 5/1984 | | A61F 5/4404 |
| EP | 2956204 | B1 * | 8/2019 | | A61M 39/10 |

*Primary Examiner* — Adam Marcetich
(74) *Attorney, Agent, or Firm* — Paul Davis

(57) ABSTRACT

The urinary catheter includes a balloon that anchors a distal end of a catheter lumen in position inside of the bladder. It includes a port open to the inner lumen at the distal end of the catheter to allow for the flow of urine from the bladder, through the catheter, and to the connected drainage bag. A drainage bag collects urine from the catheter. The drainage bag has an inlet port for receiving urine and an outlet port for draining urine from the drainage bag. There is often collection tubing that connected the catheter to the drainage bag. A lock device provides that the inlet port of the drainage bag and the outlet port of the urinary catheter remain coupled together.

20 Claims, 22 Drawing Sheets

(56) References Cited

U.S. PATENT DOCUMENTS

| | | | | |
|---|---|---|---|---|
| 4,631,056 A * | 12/1986 | Dye | A61M 39/1011 | 604/905 |
| 4,704,177 A * | 11/1987 | Vaillancourt | A61M 39/165 | 156/289 |
| 4,801,296 A * | 1/1989 | Vaillancourt | A61M 39/165 | 604/905 |
| 4,826,486 A * | 5/1989 | Palsrok | A61M 39/1011 | 24/339 |
| 4,830,914 A * | 5/1989 | Vaillancourt | A61M 39/165 | 604/905 |
| 4,834,706 A * | 5/1989 | Beck | A61M 39/1011 | 604/905 |
| 5,248,306 A * | 9/1993 | Clark | A61M 39/1011 | 604/905 |
| 5,531,695 A * | 7/1996 | Swisher | A61M 39/1011 | 604/905 |
| 5,728,061 A * | 3/1998 | Ahmed | A61M 27/006 | 604/9 |
| 5,803,509 A * | 9/1998 | Adams | A61M 39/1011 | 285/305 |
| 5,957,894 A * | 9/1999 | Kerwin | A61M 39/1011 | 604/905 |
| 10,322,247 B1 * | 6/2019 | Radcliffe, Jr. | A61M 39/1055 | |
| 11,241,566 B1 * | 2/2022 | Lindsay | A61M 39/1011 | |
| 2003/0032944 A1 * | 2/2003 | Cawood | A61F 5/4405 | 604/322 |
| 2006/0271019 A1 * | 11/2006 | Stoller | A61M 25/0017 | 604/353 |
| 2007/0225688 A1 * | 9/2007 | Goodwin | A61M 25/0017 | 604/327 |
| 2007/0244468 A1 * | 10/2007 | Kostandaras | A61M 39/08 | 604/523 |
| 2008/0171992 A1 * | 7/2008 | House | A61M 39/12 | 604/180 |
| 2010/0228231 A1 * | 9/2010 | Weigel | A61M 39/1011 | 604/535 |
| 2010/0286667 A1 * | 11/2010 | Paz | A61M 25/0017 | 604/328 |
| 2011/0087181 A1 * | 4/2011 | Bidwell | A61F 5/4404 | 604/328 |
| 2012/0089129 A1 * | 4/2012 | Engelhardt | A61M 25/02 | 604/328 |
| 2012/0172822 A1 * | 7/2012 | Gilman | A61M 39/26 | 604/328 |
| 2012/0184944 A1 * | 7/2012 | Tomes | A61F 5/4404 | 604/544 |
| 2012/0214337 A1 * | 8/2012 | Schnell | A61M 39/1011 | 439/527 |
| 2012/0232547 A1 * | 9/2012 | Cohen | A61B 18/1492 | 606/34 |
| 2013/0172840 A1 * | 7/2013 | Lampotang | A61M 39/284 | 604/327 |
| 2014/0100547 A1 * | 4/2014 | Lyons | A61M 1/3655 | 604/535 |
| 2015/0051588 A1 * | 2/2015 | Miller | A61M 39/1055 | 604/544 |
| 2015/0290449 A1 * | 10/2015 | Yanik | A61M 39/20 | 604/533 |
| 2016/0051395 A1 * | 2/2016 | Ugarte | A61F 5/4404 | 604/327 |
| 2016/0193073 A1 * | 7/2016 | Kinsey | A61F 5/4408 | 248/65 |
| 2017/0368308 A1 * | 12/2017 | Hofius | A61M 25/0097 | |
| 2018/0169377 A1 * | 6/2018 | Hickmott | A61M 25/0111 | |
| 2018/0304045 A1 * | 10/2018 | Glithero | A61M 5/1418 | |
| 2019/0314188 A1 * | 10/2019 | Barrientos | A61F 5/4408 | |
| 2019/0321587 A1 * | 10/2019 | McMenamin | A61M 25/0017 | |
| 2019/0321593 A1 * | 10/2019 | Crawford | A61M 25/0097 | |
| 2020/0269011 A1 * | 8/2020 | Carlsson | A61M 27/00 | |
| 2020/0408350 A1 * | 12/2020 | Walterspiel | F16L 58/185 | |
| 2021/0299337 A1 * | 9/2021 | Scott | A61M 1/69 | |
| 2022/0296871 A1 * | 9/2022 | Hickman | A61M 25/00 | |

* cited by examiner

CATHETER SYSTEM

BACKGROUND

Field of the Invention

This invention relates to urethral catheters, and more specifically to catheters with locking mechanisms to maintain coupling between a drainage bag and the catheter.

Description of the Related Art

The Foley catheter has been used since the 1930s in much the same form as its earlier model. The Foley catheter, in its most basic form, has a proximal portion that remains outside the body, a length that traverses the urethra, and a distal end that resides in the bladder. The Foley catheter is held in place by an inflatable balloon at the distal end, which stabilizes the device in place and prevents unintentional withdrawal from the bladder. A typical Foley catheter includes at least two lumens along its length, one lumen serving as a conduit for draining the bladder and a second lumen to inflate the balloon to hold the catheter in place in the bladder.

Various developments have added diagnostic capabilities to Foley catheters, including pressure and temperature measurement capabilities. For example, Singer, Patent Document 1, discloses a catheter having an oxygen sensing function. Both Rhea and U.S. Pat. Nos. 5,057,059 and 1993, disclose pressure sensors associated with Foley catheters. U.S. Pat. No. 6,057,059 to Noda discloses a temperature sensor associated with a Foley type catheter.

Foley catheters are widely used, low cost, can be easily put in place by healthcare professionals, and still provide further opportunities as a means of obtaining critical diagnostic information. The technology disclosed herein provides for coupling of the urinary catheter to a chosen drainage device in a leakproof fashion.

Urinary catheters are medical devices that are widely used for the management of urinary retention and incontinence. These catheters are inserted into the bladder through the urethra to drain urine. Urinary catheters are used in various settings, including hospitals, long-term care facilities, and home healthcare. It is estimated that 15-25% of hospitalized patients will receive a urinary catheter during their stay. There are also patients who will require a long-term indwelling urinary catheter to manage their bladder.

The kidneys make approximately 1.5 liters of urine daily and typical bladder capacity is 300 to 500 milliliters. When a person is unable to urinate, the problem can quickly become serious. As urine builds up in the bladder, it becomes uncomfortable, then painful. If the problem continues, the bladder can become overly full and urine can back up into a patient's kidneys, causing damage that can be permanent. When this happens, a sterile, flexible catheter tubes with lumens called a urinary catheter is inserted into the urethra (where urine leaves the body) and is gently pushed up until the end rests in a patient's bladder. The catheter then drains the urine, through attached tubing to a gravity drainage bag.

Urinary catheters are often used during surgery, as a patient can't control its bladder while under anesthesia. For this purpose, a Foley catheter is typically placed prior to surgery and keeps the bladder empty throughout. It often remains in place until the surgery is completed and a patient is awake and alert enough to begin urinating normally. A Foley catheter is a sterile urinary catheter that's intended to stay in place for an extended period of time.

A urinary catheter, regardless of type, increases the risk of a urinary tract infection. Despite the fact that sterile technique is used to insert them, the introduction of any foreign body into the urinary tract increases the risk of infection.

If pathogens enter the urinary tract, they may cause an infection. Many of the pathogens that cause a catheter-associated urinary tract infection are commonly found in a patient's intestines that do not usually cause an infection there. Pathogens can enter the urinary tract when the catheter is being put in or while the catheter remains in the bladder.

The longer a Foley catheter stays in the bladder, the greater the chance of infection. Infection is the most common problem. The catheter may let pathogens into a patient's body, where they can cause an infection of the bladder, urethra, urinary tract, or kidneys.

Catheters can leak urine, either around the catheter or through a faulty connection with the collection bag. Leaking of urine around the catheter can be due to a blockage within the catheter from a blood clot or debris. A bladder spasm, the contraction of the bladder, can also lead to urine leaking around the catheter. Mechanical kinking of the catheter itself or of the collection tubing can lead to leakage around the catheter as well.

Leakage from the connection of the catheter with the collection tubing can occur because of an incomplete fitment of the catheter to the collection tubing or a complete disconnection or uncoupling of the devices.

Catheter connectors are used to connect two sections of tubing. They are usually transparent to allow an easy observation of urine flow. Catheter Plug and Cap are designed mainly for Foley catheters. There are often problems with failure of catheter connectors to maintain a leak free connection of sections of tubing. Catheter tubing connectors are a critical component in catheter use.

Buckling, kinking or twisting during insertion make insertion significantly more difficult. Current catheters are difficult to insert and can cause significant discomfort to the patient and frequently suffer from reduced flow of urine through them due to mechanical deformation during insertion or use. Currently tubular components of catheters tend to become uncoupled from the collection tubing which is connected to the catheter drainage bag. The present invention fulfils a long-felt need for a catheter that does not suffer from these defects.

Additionally, there is a need for a catheter that does not become uncoupled from the catheter drain bag, there is a further need for a catheter to not become kinked or block fluid flow.

SUMMARY

An object of the present invention is to provide a catheter coupled to a drainage bag so that the two remain coupled when the catheter or drain bag moves.

Another object of the present invention is to provide a closed system with a locking/tight/secure mechanism that couples a catheter to attach/detach with a drain bag.

A further object of the present invention is to provide a catheter coupled to a drainage bag that remain coupled irrespective of body movement.

Yet another object of the present invention is to provide a catheter coupled to a drainage bag with a two-step locking mechanism.

The urinary catheter includes a balloon that anchors a distal end of a catheter lumen in position inside of the bladder. It includes a port open to the inner lumen at the distal end of the catheter to allow for the flow of urine from the bladder, through the catheter, and to the connected drainage bag. A drainage bag collects urine from the catheter. The drainage bag has an inlet port for receiving urine and an outlet port for draining urine from the drainage bag. There is often collection tubing that connected the catheter to the drainage bag. A two-step lock device provides that the inlet port of the drainage bag and the outlet port of the urinary catheter remain coupled together. The urinary catheter tube is made of a flexible material, and/or includes one or more coiled sections that provide for movement of at least a portion of the urinary catheter relative to the drainage bag.

DETAILED DESCRIPTION

Figure 1:
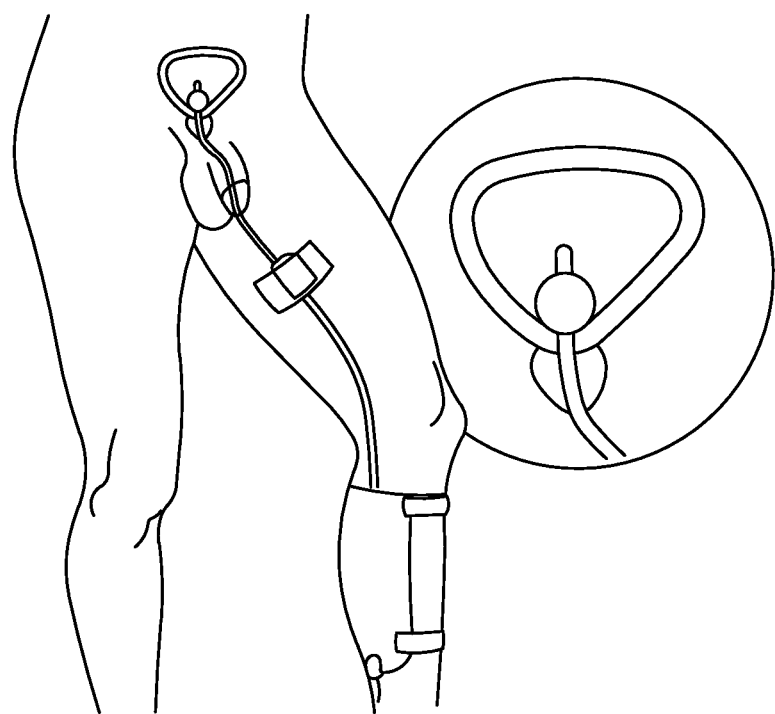
FIGS. 1-5 illustrate one embodiment of a flexible catheter.
Figure 2:
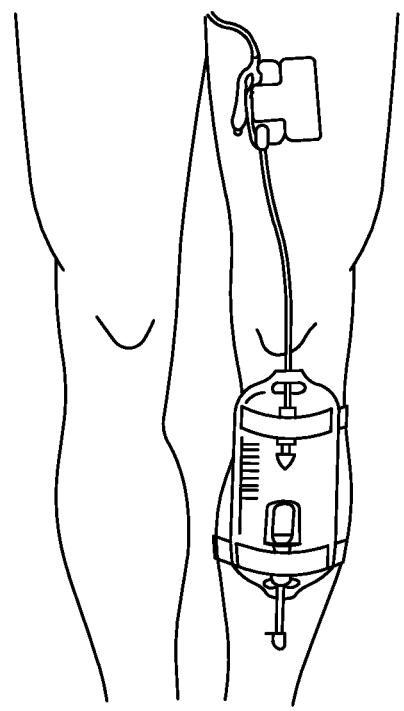
Figure 3:
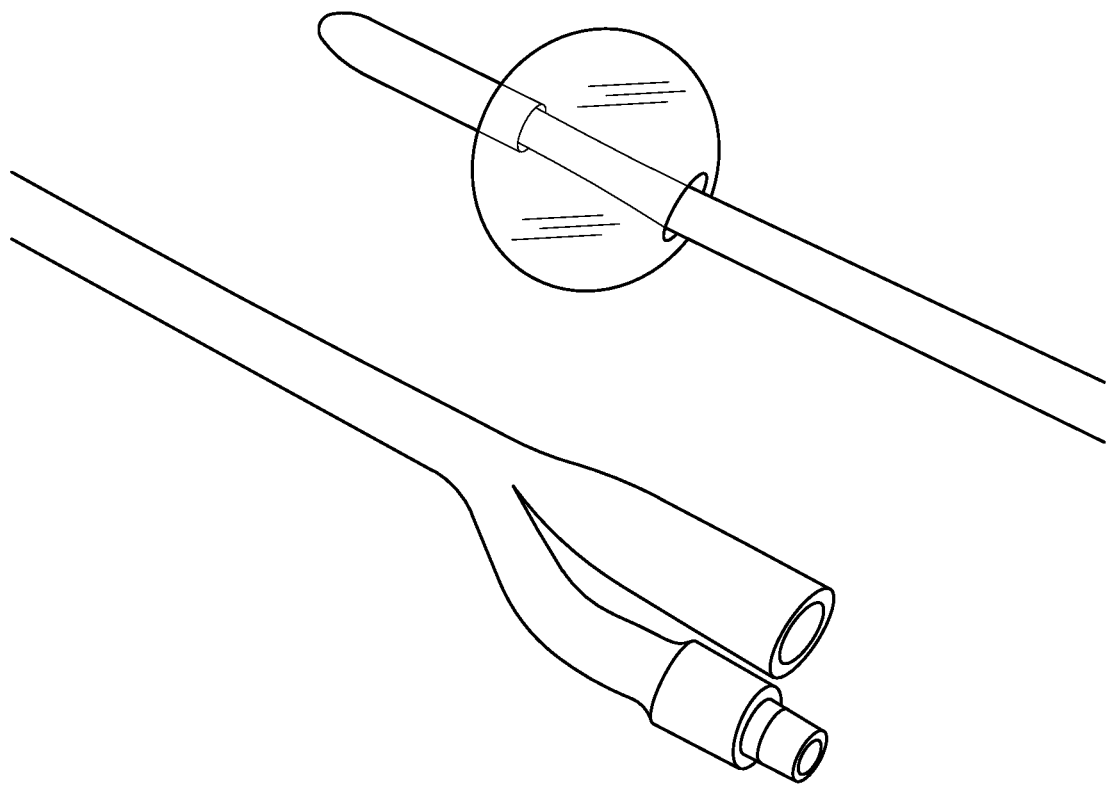
Figure 4:
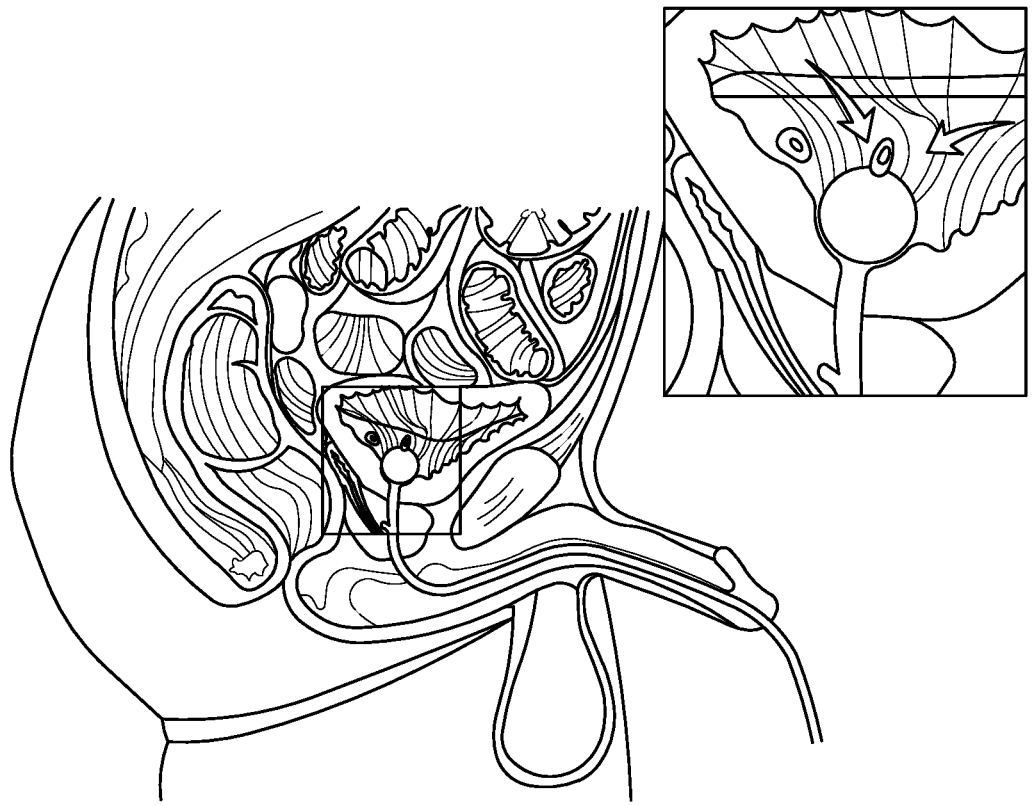
Figure 5:
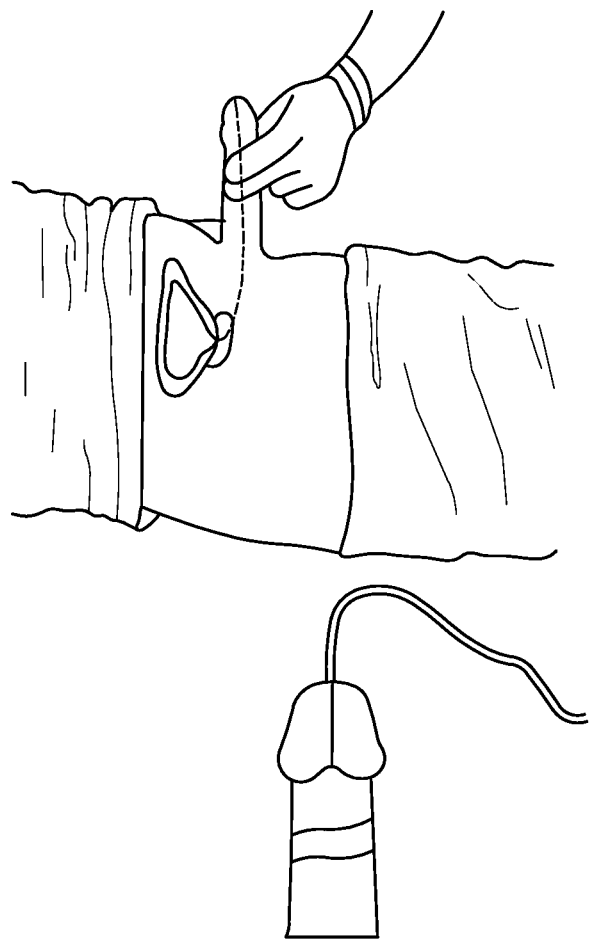

As illustrated in FIGS. 1-5, in one embodiment, a flexible catheter 10 is provided that includes one or more a hollow, partially or fully flexible catheter tubes, generally 12, that can be a single tube, multiple tubes 12(*a*)-(*c*), with lumens that collect urine from the bladder and leads to a drainage bag 14. As a non-limiting example, drainage bag 14 can be expandable, flexible, be a urinary leg bag with top and bottom leg attachments that can be flexible, adjustable, and the like. In one embodiment, drainage bag 14 reduces fluid back pressure by avoiding the formation of dependent loops, and can include low aspect ratio collection receptacles that rest on a flat surface to improve fluid flows and/or minimize back-pressures exerted by collected fluids. Flexible catheter 10 is kept in place by a balloon that is inflated in bladder with sterile water the catheter is inserted. Included as an inflatable balloon, inflated through an inflation port when the inflatable balloon is positioned in the bladder.

Catheter 10 includes a single flexible catheter tube 12, multiple flexible catheter tubes 12(*a*)-(*c*). In one embodiment, flexible catheter tubes 12, 12(*a*)-(*c*) can be made of a stretched thermoplastic material. The thermoplastic material can be extrudable. As a non-limiting example, the thermoplastic material can be (a) from 40 to 70 percent by weight of an elastic composition which comprises: from 50 to 99.5 percent by weight of a block copolymer having thermoplastic rubber characteristics with a central, rubbery polyolefin block and terminal blocks of polystyrene, and optionally including up to about 45 percent by weight of polypropylene, plus from 0.5 to 10 percent by weight of a cross-linked organic silicone elastomer; and (b) from 30 to 60 percent by weight of a hydrophobic oil-type plasticizer to provide the desired degree of softness to said elastic composition.

Figure 6:
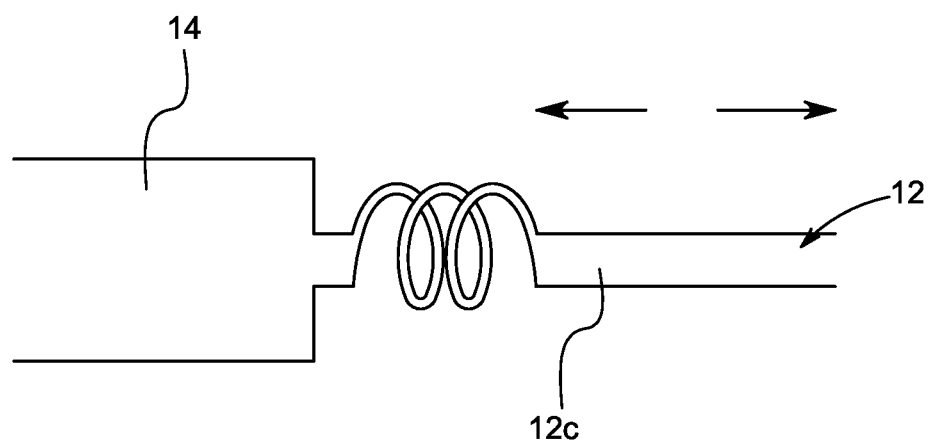
FIG. 6 illustrates one embodiment of a flexible catheter partially or wholly coiled to provided additional catheter length that is stretchable to provide movement.
Figure 7:
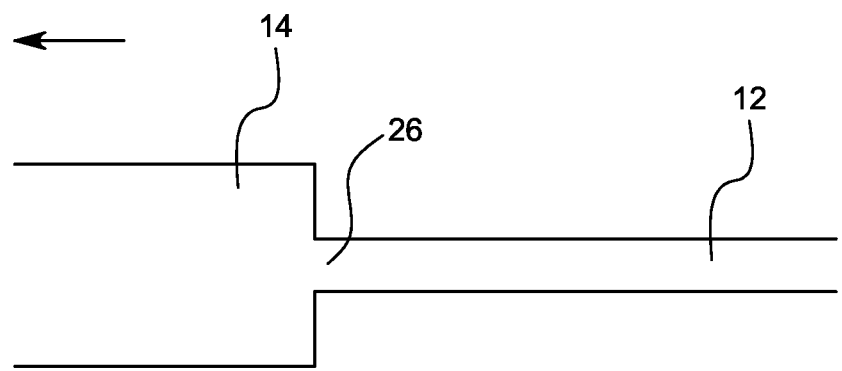
FIG. 7 illustrates one embodiment of a flexible catheter made of a suitable material that is able to stretch when drainage bag moves in directions towards or away a drainage bag.

In one embodiment, all or a portion, particularly the end section of flexible catheter 12 and/or 12(*c*) can be partially or wholly coiled to provided additional catheter length that is stretchable to provide movement, see FIG. 6. The coiled portion can readily extend and contract to relieve tension on the catheter 10. In one embodiment, flexible catheter tube 12, 12(*a*)-(*c*) is movable with respect to drain bag 14, see FIG. 6. As a non-limiting example, distal end of 12(*c*) can be coupled to drainage bag inlet port 22 with a flexible, expandable outlet port 26. All or all of a portion of urinary catheter 10, and the like and also made of a suitable material that is able to stretch when drainage bag moves in directions towards or away from outlet port 26, see FIG. 7.

Common indications for placing a urinary flexible catheter in a patient include: (i) acute or chronic urinary retention, both mechanical such as in the case of benign prostatic hypertrophy or non-mechanical such as in spastic bladder neck; (ii) the need to measure the urine output in critical care patients; (iii) incontinence; and (iv) patients post bladder or gynecological surgery.

Figures 8, 9:
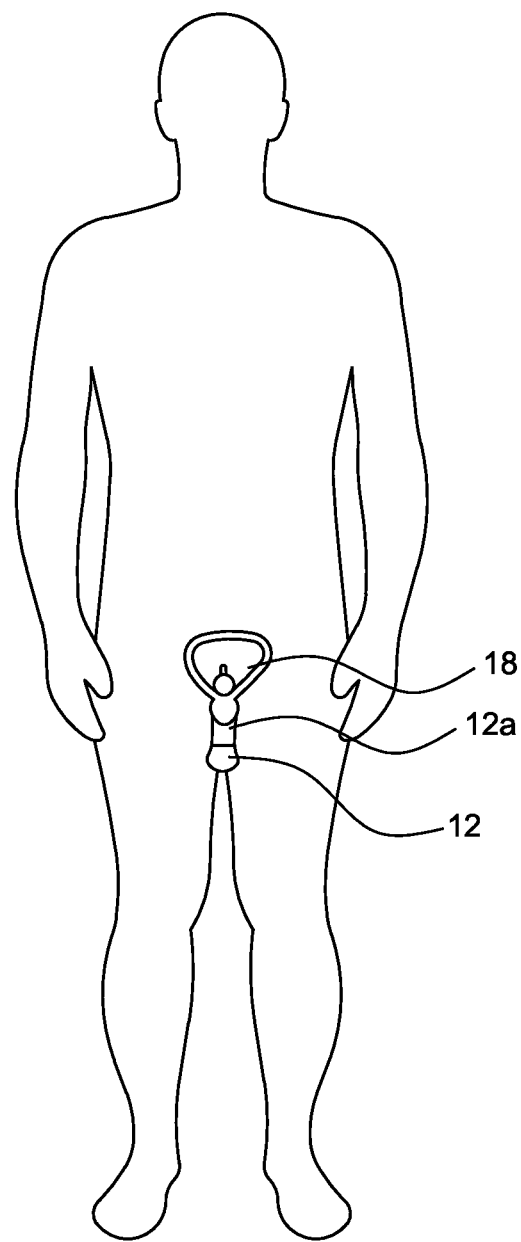
FIGS. 8 and 9 illustrates a proximal flexible catheter tube is inserted into a patient

As illustrated in FIGS. 8 and 9, in one embodiment, proximal flexible catheter tube 12(*a*) is inserted into a patient, in this embodiment, the penis, which can be held at a selected angle, for example 90 degrees. Catheter 12(*a*) or a single flexible catheter tube is advanced into the patient's urinary meatus. There may be resistance at the urethral sphincter or the prostate. It is recommended that the advancement be paused to allow the sphincter to relax. The penis is then lower and the flexible catheter tube 12(*a*) continues to advance.

Catheter 10 can be: an indwelling catheter; a condom catheter; intermittent self-catheter and the like. Dimensions of catheter 10 can be 10 Fr (3.3 mm) to 30 Fr (10 mm), and color-coded by size and have a solid color band on the outer end of the balloon inflation tube for easy size identification. Size 12 Fr is large enough to relieve urinary obstruction in most adults, although practitioners typically choose size 14 to 16 Fr for initial catheterization. As a non-limiting example, suitable dimensions of catheter 10, more particularly of flexible catheter tubes 12 can be as follows:

| Color | Size French | Size in Millimeter |
| --- | --- | --- |
| Light Green | 6 | 2.0 mm |
| Light Blue | 8 | 2.7 mm |
| Black | 10 | 3.3 mm |
| White | 12 | 4.0 mm |
| Green | 14 | 4.7 mm |

-continued

| Color | Size French | Size in Millimeter |
|---|---|---|
| Orange | 16 | 5.3 mm |
| Red | 18 | 6.0 mm |
| Yellow | 20 | 6.7 mm |
| Purple | 22 | 7.3 mm |
| Blue | 24 | 8.0 mm |
| Black | 26 | 8.7 mm |

Figure 10:
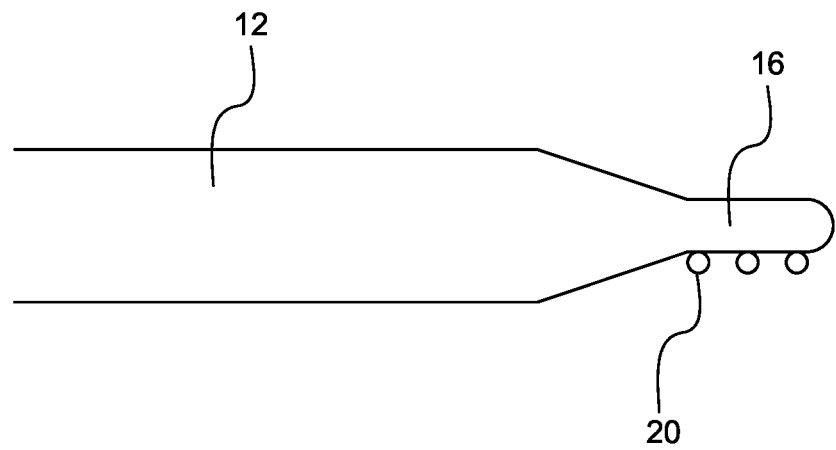
FIG. 10 illustrates one embodiment of insertion of a proximal end of a flexible catheter inserted into the urethra to reach the bladder.

In one embodiment a flexible catheter 10 is provided. Flexible catheter 10 can include an insertion tip 16, FIG. 10, that is advanced by a patient's urethra. In one embodiment, insertion tip 16 is a narrow proximal end of flexible catheter 10 that inserts into the urethra to reach the bladder 18. Insertion tip 16 includes one or more draining holes/eyelets 20 in that receive fluids, including urine, from the bladder 18. Draining holes 20 are small holes in proximal flexible catheter tube 12, which are positioned on or very near insertion tip 16 to make urine draining easy. Flexible catheter drainage holes 20 are sometimes referred to as drainage holes or flexible catheter eyes 20

Figure 11:
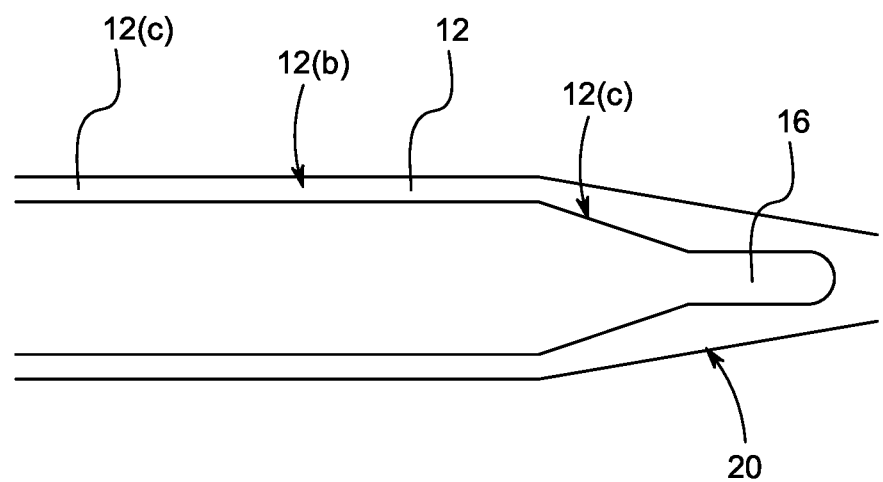
FIG. 11 illustrates a flexible catheter with only one tube extending from the bladder to the drainage bag.
Figure 12:
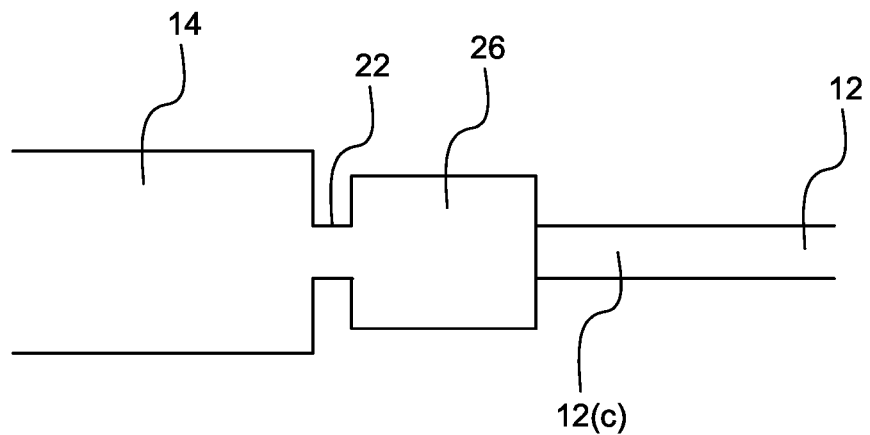
FIG. 12 illustrates an outlet port sufficiently coupled to the inlet so that the two remain coupled when catheter moves or drain bag moves.

As illustrated in FIG. 11, a first flexible catheter tube 12(a), with lumen is provided. In various embodiments a plurality of flexible catheter tubes 12(a)-(c), with lumens, are included and can have one or more intermediate flexible catheter tubes 12(b) with lumens, a distal flexible catheter tube 12(c) with lumen and the like. Flexible catheter 10 can have only one flexible catheter tube 12, extend from the bladder 18 to drainage bag 14. It will be appreciated that all catheter tubes can be flexible, expandable, moveable, and the like. Flexibility reduces the occurrence of a catheter tube 12 from being in a kinked, non-flowing positioned, obstructed, and bent as to restrict urine flow Drain bag 14 includes an inlet port 22 for coupling/attaching to a distal end of flexible distal catheter 12(c). Drain bag 14 also includes a drainage outlet port 24 for draining collected urine and the like from drainage bag 12. Distal end of flexible distal catheter 12(c) includes an outlet port 26 to couples to inlet port 22. Outlet port 26 is sufficiently coupled to inlet port 22 so that the two remain coupled when catheter 10 moves or drain bag moves, FIG. 12. They do not become disconnected from a patient's body motion and/or movement. This is more fully discussed below.

In one embodiment, flexible catheter 10 can be a Foley flexible catheter, straight intermittent flexible catheter, a closed system flexible catheter kit, and the like. As a non-limiting example, flexible catheter 10 can have a variety of insertion tips 16, such as a straight tip, a crude tip and the like. The decision as to the type of insertion tip 12 to use is often made by the physician, the physician and patient, the nurse, physician's assistant, caregiver and the like. Insertion tip 16 can be at one end of first flexible catheter tubes with lumens 12(a)-12(c) can be flexible and/or include a spiral. As a non-limiting example, flexible catheter 10 can include only the first tubes 12 with a lumen extending from the bladder to the draining bag 14. Flexible catheter tubes 12(a)-(c), with lumens, as well as lumen 12 can be made of a variety of materials, including but not limited to: assorted polymers, polymer-metal composites polyamide (nylon), polyether block amide, polyurethane, polyethylene terephthalate, and polyimides.

In one embodiment, flexible catheter tubes 12, which can be 12(a)-(c) can be coated or impregnated with a variety of materials 29 for various purposes including but not limited to materials that provide: protect against infection, case the discomfort of insertion, and the like. As a non-limiting example, tubes 12(a)-(c) can include one or more lumens inside and outside lumen walls. These walls ben be coated or impregnated on the inside and outside lumen walls with biomimetic surface 29 to prevent bacterial or other microbial growth. In another embodiment, the surfaces of the tubes 12 and/or lumen walls impregnated and/or coated with antibiotics, antibacterial or coated with biocompatible materials that prevent bacterial overgrowth, such as silver or copper.

Figure 13:
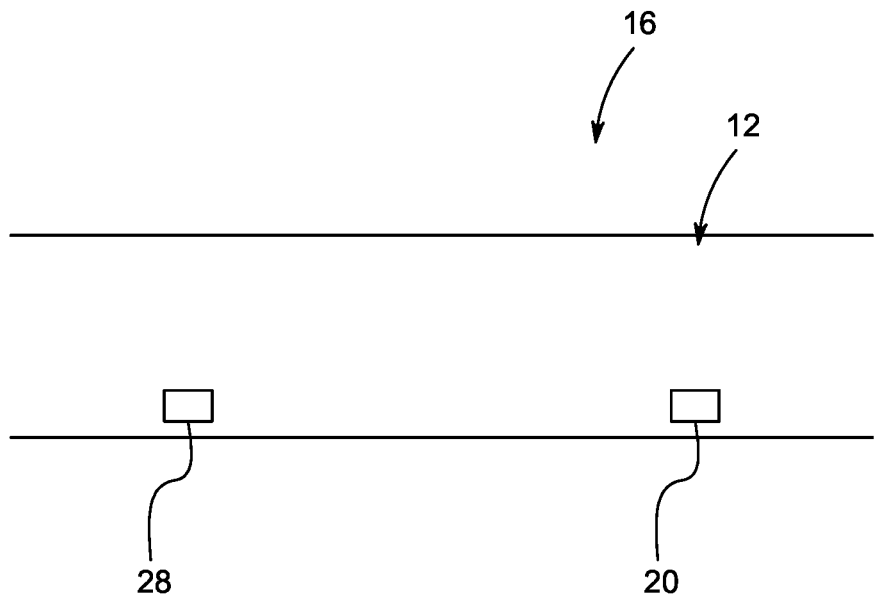
FIG. 13 illustrates a catheter with one or more sensors

In one embodiment, catheter 10 includes one or more sensors 28, FIG. 13, that sense physiological data from a patient's urinary tract. As a non-limiting example, physiological data can be collected by high fidelity pressure sensing and conversion into signals suitable for processing. This can include sensing of temperature and clinically important analytes.

In addition, an inside wall of an inner lumen can be coated with a material that has low friction to enhance urine flow. This material can include but is not limited to: plastic, PET, a naturally occurring latex, or synthetic latex material. As a non-limiting example, outer surface of tubes 12 can be coated with a material designed to reduce friction so that catheter 10 can be inserted easily without undue force or trauma to the urethra or the bladder or any other body part. In one embodiment, the tube lumens can be coated on the outer surface with a material that enhances mucosal growth.

In one embodiment, an introducer can be used to facilitate insertion of catheter 10 into the urinary tract.

In one embodiment, flexible catheter 10 is made more comfortable. This can be achieved by polishing and recessing drainage holes 20, which can reduce friction and irritation in the delicate urethral tissues. As a non-limiting example, flexible catheter tubes 12 can be silicone-elastomer, coated after insertion, and the like.

Figure 14:
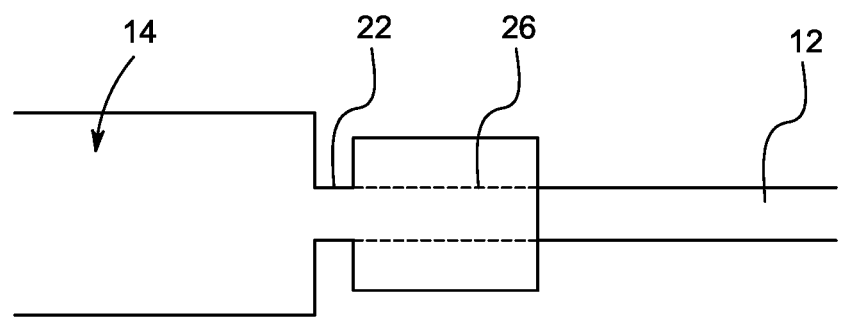
FIG. 14 illustrates inlet and outlet ports remaining coupled irrespective of body movement.

As previously stated, and as illustrated in FIG. 14, inlet and outlet ports 22 and 26 remain coupled irrespective of body movement. An infusion cleaning port 30 for cleaning distal end of flexible catheter 12(c) for can included.

Figure 15:
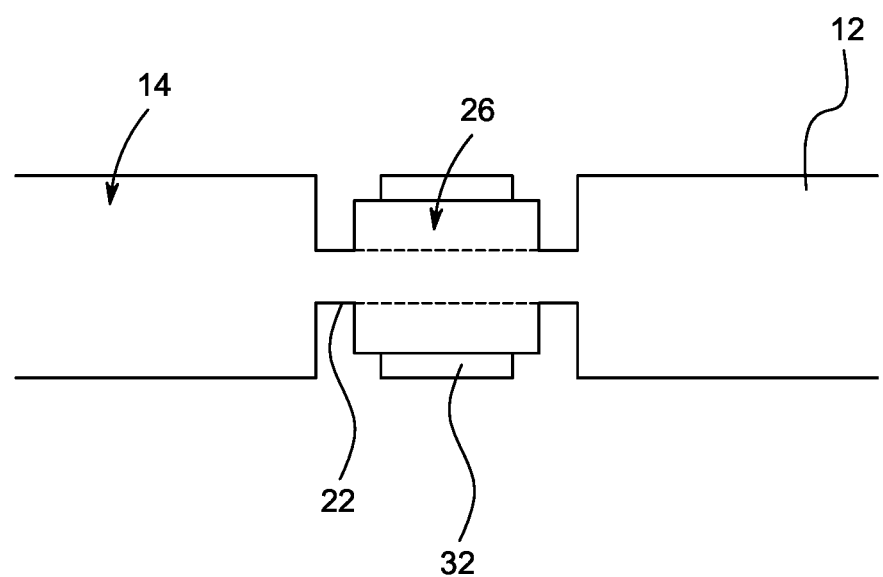
FIG. 15 illustrates an embodiment with two ports with a locking mechanism.

In one embodiment, ports 22 and 26 remain in a locked engagement and can have a locking mechanism 32, FIG. 15, positioned around exteriors or interiors of outlet ports 24 and 26. This provides a closed system with a locking/tight/secure mechanism 32 that couples a urinary catheter 10 to attach/detach with drain bag 14.

Figure 16:
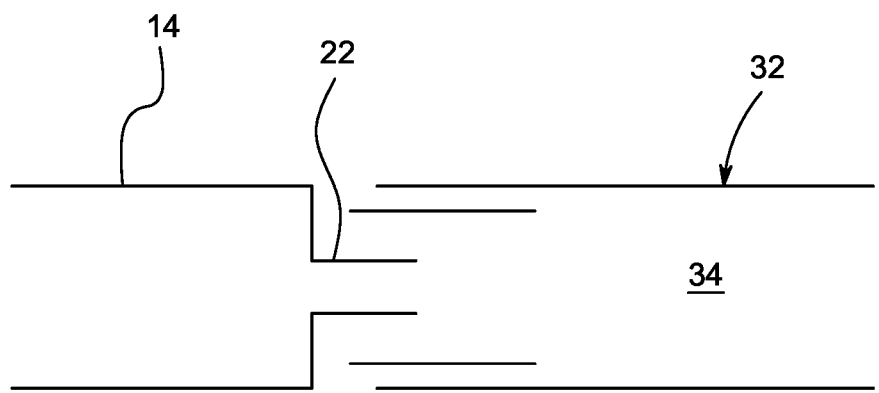
FIG. 16 illustrates inlet and outlet ports each have a plurality of ridges that engage with each other to provide a locking arrangement.

In one embodiment, locking mechanism 32 provides a compression force to outlet ports 24 and 26, but still allows passage of the fluid, urine, into drain bag 14. A variety of locking mechanisms 32 can be used including but not limited to: a bore connector, a series-to-twist coupling, (SMC), luer, SMC connector that allows rotation and movement and prevents kinking, one or more series twist-to-connect couplings, twist lock, swivel-snap connectors, locking connectors, windings, brackets, flip locks, lockout locks, pop locks, telescopic tube locks, Locking & telescoping mechanisms for composite tubes Flip lock clamps & twist lock rings Button clips & ball lock pins, push button telescoping tube locks, telescoping tube clamps around telescoping tubing locks, tubular locks, micro-tube cap locks, telescoping tube adjusters, pin clips, lock nuts, and the like. As illustrated in FIG. 16, in one embodiment, a hollow pipe 32 and a group of telescopic sleeves 34 are used for coupled. The telescopic tube can be a fixed sleeve fixedly arranged at an end part of the closed first end of the hollow tube to communicate the inner cavity of the hollow tube with the outside, and a sliding sleeve which is sleeved with the fixed sleeve in a sliding manner.

As a non-limiting example, locking mechanism 32 can be a twist-lock 32, snap-lock 32, luer-lock 32, clamp-lock 32 and the like.

In various embodiments, locking mechanism 32 can be formed of any desired material, giving the locking mechanism 32 a desired amount of flexibility and/or compressibility. Locking mechanism 32 can be formed of silicone or other flexible polymeric material. Silicone provides rubber-like properties and can frictionally engage ports 22 and 26 with compression without interrupting the flow of urine. As a non-limiting example, locking mechanism 32 is coated with a material having a high coefficient of friction to enhance the frictional engagement.

In one embodiment, locking mechanism 32 can be in a first position in which the flexible catheter distal tube 12(*c*) is free to move longitudinally via locking mechanism 32. This movement reduces the chance that catheter distal tube 12(*c*) disengages from inlet port 22 of drain bag 14. In one embodiment, locking mechanism 32 can move to a second position in catheter distal tube 12(*c*). allowing movement, and produces less stress on its engagement with drain bag 14.

Figure 17:
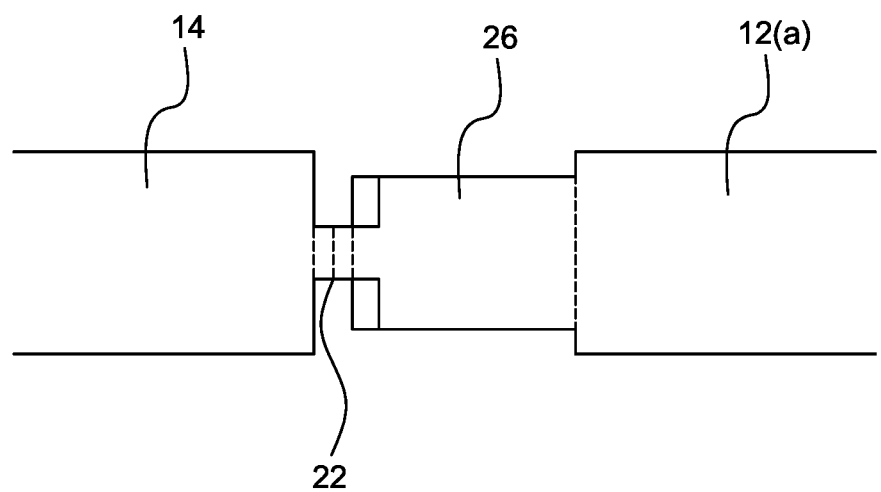
FIG. 17 illustrates the inlet and output ports each having windings similar to a screw.

In one embodiment, illustrated in FIG. 17 inlet port 22 and outlet port 26 each have a plurality of ridges that engage with each other to provide a locking arrangement. In another embodiment, illustrated in FIG. 17, inlet port 22 and outlet port 26 each have a plurality of windings, such as in a screw, and are coupled together with engagement of the windings. In other embodiments, the drain bag 14 is locked to catheter distal tube 12(*c*) with bends notches, recesses, and the like.

As a non-limiting example, an improved locking mechanism 32 is provided that prevents leaks of urine, is easy for a patient or care giver to use, is compatible a variety of different drain bags 14 and urinary catheters 10 and the like. In one embodiment, locking mechanism 32 is positioned at a place at drain bag 14 so as not to cause any irritation to the patient's skin. Locking mechanism 32 can have a configuration that is substantially smooth, without any rough edges. Locking mechanism 32 can be made of the same material as tube 12(*c*).

As a non-limiting example, locking mechanism 32 can be a two-step lock 32 to provide greater engagement between urinary catheter 10 and drain bag 14. This results in a reduction and/or elimination of urine leakage. In one embodiment, a connector 33 is used to couple and/or insert, urinary catheter 10 into drain bag 14. In a second step, urinary catheter 10 then engagers with connector 18 to lock in place, as illustrated in FIG. 18 This is done by using locking mechanism 32 that ensures urinary catheter 10 does become disconnected from drain bag 14, partially when the patient moves.

Figure 18:
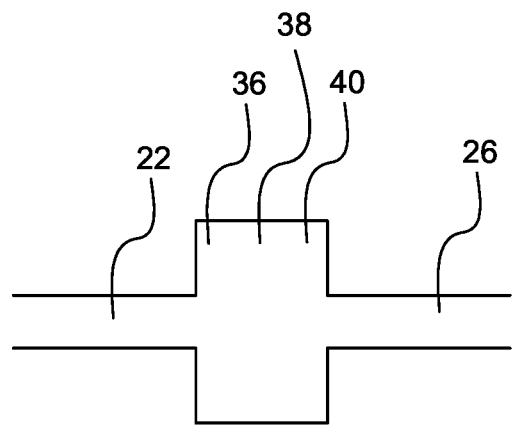
FIG. 18 illustrates a two-step locking mechanism, with a connector and lock.

In various embodiment, FIG. 18, locking mechanism can be a twist-lock 36, snap-lock 38, clamp-lock 40, luer lock 42, and the like. Twist-lock 36 is configured to prevent over-twisting, and under-twisting when locking, and no or little damage to connector 33 and tube 12(*c*), more particularly inlet port 22 and outlet port 26 Under-tightening results in inadequate coupling, and causes leaking.

Figure 19A:
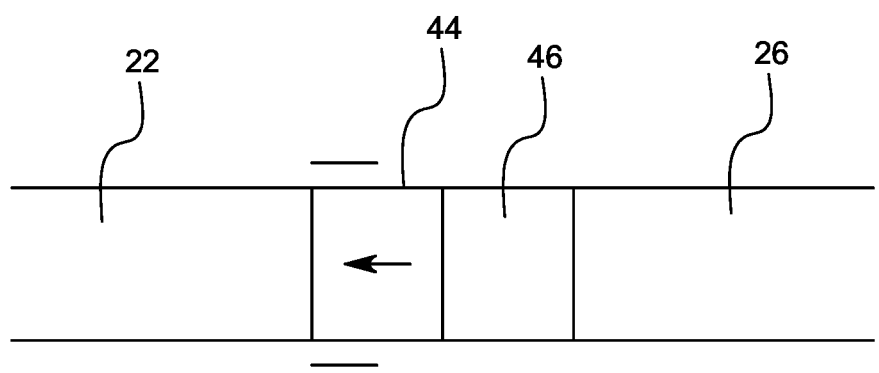
FIGS. 19 (*a*) and 19 (*b*) illustrate one embodiment of a twist-lock, with male and female connectors.
Figure 19B:
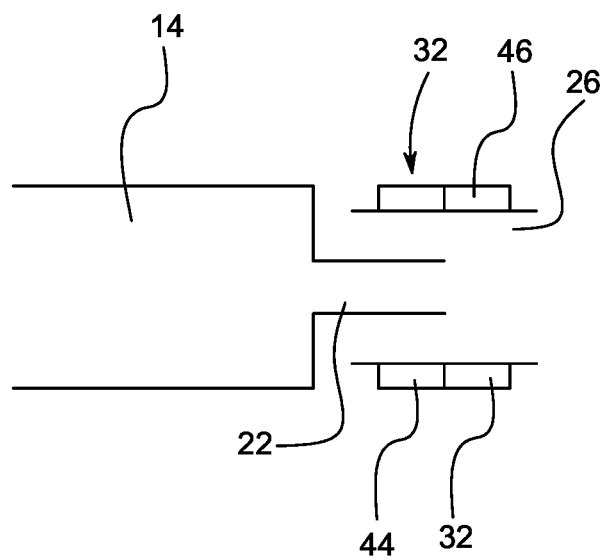

FIGS. 19 (*a*) and 19 (*b*) illustrate one embodiment of a twist-lock 32, with male and female connectors 44 and 46. Male connector 44 has a threaded end that is inserted into female connector 46. Connectors 44 and 46 and then twisted together. This creates a seal.

Figure 20:
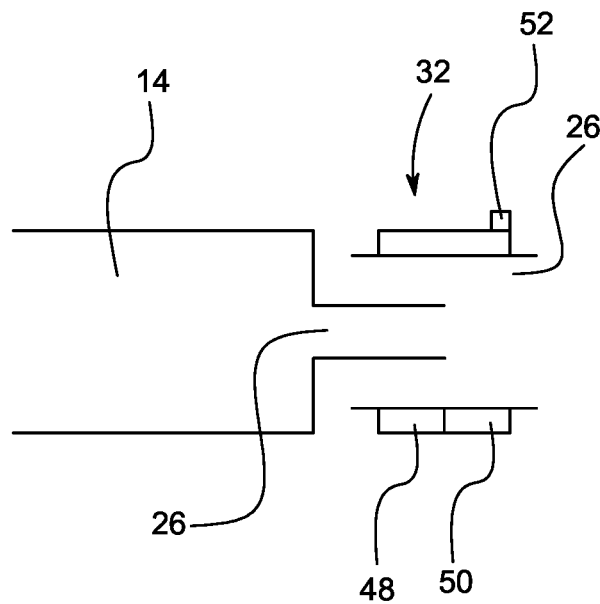
FIG. 20 illustrates one embodiment of a snap-lock includes male and female connectors.

As illustrated in FIG. 20, snap-lock 32 includes male and female connectors 48 and 50. Male connector 48 has a protruding tab or button 52 that snaps into a corresponding slot of female connector 50. Connectors 48 and 50 are pushed together until tab or button 52 snaps, creating a seal.

Figure 21:
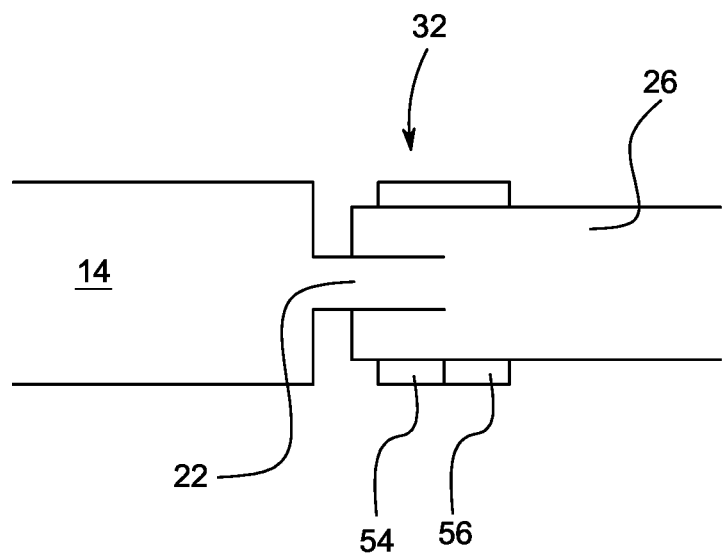
FIG. 21 illustrates one embodiment of a luer lock.

Referring to FIG. 21, luer-lock 32 includes male and female connectors 54 and 56, Female connector 56 has a tapered opening with threads that match those on male connector 54. The threads secure connectors 54 and 56, creating a seal.

Figure 22:
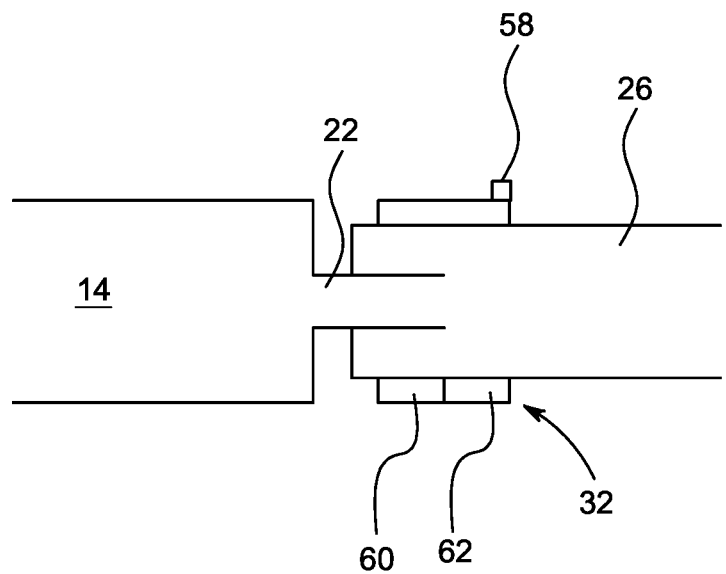
FIG. 22 illustrates one embodiment of a clamp lock.

Referring to FIG. 22, clamp lock 32 includes male and female connectors 58 and 60. Male connector 58 is inserted into female connector 60. Male connector 58 can include a tapered end. A sliding mechanism 62 is used for the coupling, created a seal.

Locking mechanism 32 can be added to an existing catheter, or be a part of catheter system 10.

It is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples s provided in the present disclosure.

The invention claimed is:

1. A urinary catheter, comprising:
   a catheter with a urinary catheter tube with a lumen, a proximal end, a distal end and a balloon coupled to the proximal end, the balloon configured to be positioned in an interior of a bladder, the proximal end configured to provide flow of urine from the bladder through the catheter lumen;
   a leg strap;
   a drainage bag having an inlet port for receiving urine from the catheter lumen and an outlet port for draining urine from the drainage bag, the drainage bag not including an extending tubing that extends from the inlet port, the drainage bag coupled to the leg strap and configured to be attached to a patient's leg;
   the urinary catheter tube including the proximal end, the proximal end-having a plurality of urine draining holes that receive urine from the bladder and allow it to be transported to and through the urinary catheter tube, the urinary catheter tube being made of a flexible material, or including one or more coiled sections that provide for movement of at least a portion of the urinary catheter relative to the drainage bag, the urinary catheter tube having an output port at the distal end of the urinary catheter tube coupled to the inlet port of the drainage bag; and
   wherein the inlet port of the drainage bag and the outlet port of the urinary catheter tube are locked together by a locking mechanism without a pleated segment and not part of the drainage bag or the catheter, the locking mechanism positioned in a completely surrounding relationship to surround an entirety of an exterior of the output and inlet ports, the locking mechanism preventing leakage of urine from the outlet port and the inlet port, with the inlet port directly connecting to the outlet port at the drainage bag, the locking mechanism providing a compression force applied by the locking mechanism to all of the exteriors of the output and inlet ports, allowing for longitudinal movement of one or more of the output port and inlet port along with the locking mechanism when the patient's leg moves more than a predetermined distance.

2. The urinary catheter of claim 1, wherein the urinary catheter tube includes a single catheter tube or a plurality of coupled catheter tubes.

3. The urinary catheter of claim 1, wherein the inlet port of the drainage bag includes a plurality of ridges that engage with a plurality of ridges of the outlet port of the catheter tube, providing a locking arrangement.

4. The urinary catheter of claim 1, wherein the inlet port of the draining bag includes a plurality of windings that engage with a plurality of windings of the outlet port of the catheter tube, providing a locking arrangement.

5. The urinary catheter of claim 1, wherein the inlet port of the drain bag is engageably coupled to the output port of catheter tube with one or more of bends, notches, and recesses.

6. The urinary catheter of claim 1, wherein the urinary catheter tube is one or more of a hollow, partially or fully flexible catheter tube(s) that can be a single tube, or multiple tubes with lumens that collect urine from the bladder and are coupled to the drainage bag.

7. The urinary catheter of claim 1, wherein the drainage bag is expandable or flexible.

8. The urinary catheter bag of claim 1, wherein the drainage bag is a urinary leg bag with top and bottom leg attachments that can be flexible and adjustable.

9. The urinary catheter of claim 1, wherein the drainage bag is configured to reduce fluid back pressure.

10. The urinary catheter of claim 1, further comprising:
the balloon is configured to be inflated through an inflation port when the balloon is positioned in the bladder.

11. A urinary catheter including a balloon that anchors a proximal end of a catheter lumen configured to be positioned in an interior of a bladder, the proximal end providing flow of urine from the bladder through the catheter lumen, comprising:
a drainage bag for collecting urine from the bladder, the drainage bag having an inlet port coupled to the catheter lumen and an outlet port, the inlet port receiving urine and the outlet draining urine from the drainage bag, the drainage bag having the inlet port for receiving urine without a extending tubing, the drainage bag coupled to a leg strap that is configured to be attached to a patient's leg;
a urinary catheter tube with a lumen and including the proximal end configured to be positioned in the bladder, the proximal end having a plurality of urine draining hole that receives urine from the bladder and allow it to be transported to and though the urinary catheter tube, the urinary catheter tube being made of a flexible material, or including one or more coiled sections;
wherein the inlet port of the drainage bag and the outlet port of the urinary catheter tube are locked together by a lock device without a pleated segment and is not part of the drainage bag or the catheter, the lock device preventing leakage of urine from the outlet port and the inlet port, with the inlet port directly connecting to the outlet port at the drainage bag, the lock device and positioned in a completely surrounding relationship at an exterior of the output and inlet ports providing a compression force that is applied by the lock device locking mechanism to all sections of the output and inlet ports, providing a durable coupling of the inlet port and the outlet port and allows for longitudinal movement of one or more of the output port at the distal end of the urinary catheter and inlet port along with the lock device when the a patient's leg moves a predetermined distance.

12. The urinary catheter of claim 11, wherein at least a portion of the urinary catheter tube is made of a thermoplastic material.

13. The urinary catheter of claim 12, wherein at least a portion of the thermoplastic material includes a block copolymer.

14. The urinary catheter of claim 11, wherein a flexible material or one or more coiled sections of the urinary catheter tube extend and contract to relieve tension on the urinary catheter.

15. The urinary catheter of claim 11, wherein at least a portion of the urinary catheter tube is movable or extendable with respect to the drainage bag.

16. The urinary catheter of claim 11, wherein the distal end of the urinary catheter tube is coupled to the drainage bag inlet port with a flexible, expandable outlet port.

17. The urinary catheter of claim 11, wherein the urinary catheter tube is configured such that the drainage bag can move towards or away from the outlet port.

18. The urinary catheter of claim 11, wherein the inlet port of the draining bag includes a plurality of windings that engage with a plurality of windings of the outlet port of the catheter tube, providing a locking arrangement.

19. The urinary catheter of claim 11, wherein the drainage bag is expandable or flexible.

20. The urinary catheter bag of claim 11, wherein the drainage bag is a urinary leg bag with top and bottom leg attachments that can be flexible and adjustable.

* * * * *